(12) United States Patent
Kriz

(10) Patent No.: US 6,319,209 B1
(45) Date of Patent: Nov. 20, 2001

(54) DISPOSABLE TEST VIAL WITH SAMPLE DELIVERY DEVICE FOR DISPENSING SAMPLE INTO A REAGENT

(75) Inventor: Dario Kriz, Malmö (SE)

(73) Assignee: European Institute of Science, Lund (SE)

( * ) Notice: Subject to any disclaimer, the term of this patent is extended or adjusted under 35 U.S.C. 154(b) by 0 days.

(21) Appl. No.: 09/379,158

(22) Filed: Aug. 23, 1999

(51) Int. Cl.$^7$ .................................................. A61B 5/00
(52) U.S. Cl. ............................................. 600/583; 606/181
(58) Field of Search ................................... 600/562, 564, 600/569, 570, 572, 573, 576, 583; 606/181

(56) References Cited

U.S. PATENT DOCUMENTS

| | | |
|---|---|---|
| 3,045,494 | 7/1962 | Gerarde . |
| 3,640,268 * | 2/1972 | Davis ..................... 600/570 |
| 3,648,684 | 3/1972 | Barnwell et al. . |
| 3,874,367 | 4/1975 | Ayres . |
| 3,926,521 | 12/1975 | Ginzel ..................... 356/39 |
| 4,376,634 * | 3/1983 | Prior et al. ............... 600/572 |
| 4,886,071 | 12/1989 | Mehl et al. . |
| 4,935,020 | 6/1990 | Broden . |
| 5,266,266 | 11/1993 | Nason ...................... 422/58 |
| 5,533,993 | 7/1996 | Maier . |
| 5,569,286 | 10/1996 | Peckham et al. . |
| 5,613,978 | 3/1997 | Harding . |
| 5,702,366 | 12/1997 | Lichtenberg . |
| 5,827,675 | 10/1998 | Skiffington et al. ........ 435/8 |
| 5,830,154 * | 11/1998 | Goldstein et al. .......... 600/572 |
| 5,833,630 | 11/1998 | Kloth ..................... 600/576 |

OTHER PUBLICATIONS

Erlich, Henry A. (Editor), PCR Technology, Principles and Applications for DNA Amplification, 1989 (p.4).

* cited by examiner

*Primary Examiner*—John P. Lacyk
*Assistant Examiner*—Pamela Wingood
(74) *Attorney, Agent, or Firm*—Knobbe Martens Olson & Bear LLP

(57) ABSTRACT

A disposable body fluid or tissue collection vial is disclosed. The vial has a sample accessing tool and a sample delivery member for dispensing a sample of body fluid or tissue into a reagent. The vial also has a base, a sample delivery sleeve, a sample accessing sleeve, and a cap. The sample delivery sleeve detachably attaches to the base, the sample accessing sleeve detachably attaches to the sample delivery sleeve, and the cap detachably attaches to the sample accessing sleeve. The base may contain one or more reagents suitable for diagnostic or other uses.

18 Claims, 4 Drawing Sheets

DISPOSABLE TEST VIAL WITH SAMPLE DELIVERY DEVICE FOR DISPENSING SAMPLE INTO A REAGENT

FIELD OF THE INVENTION

The present invention relates generally to diagnostic tools and more specifically to a disposable body fluid or tissue collection vial having a sample accessing tool and a sample delivery member for dispensing a sample of body fluid or tissue into a reagent.

BACKGROUND OF THE INVENTION

Several tests are carried out daily on body fluids or tissue taken from patients in hospitals and clinics in order to establish the patient's health or disease state. Blood, semen, saliva, spinal fluid, lymph, perspiration, and urine are body fluids that may be tested to determine a subject's condition. Skin cells, cheek cells, biopsy tissue, and fecal samples are also routinely examined to make medical diagnosis. In addition, several diagnostic procedures are conducted on body fluids and tissues taken for the purpose of forensic analysis.

In the blood sampling field, many diagnostic systems are employed. One of the more commonly used systems involves the collection of blood from a vein through a needle assembly into an evacuated container. The evacuated container provides a pressure differential to facilitate the flow and collection of blood through the needle assembly into the container (Barnwell et al., U.S. Pat. No. 3,648,684). Most procedures of blood sampling and diagnostic testing require that blood be drawn into a vacuum tube that is then removed; subsequently portions of the sample are taken from the tube for diagnostic analysis.

Vessels that contain pre-determined amounts of reagents for use in diagnostic testing are well known. The use of such implements, however, requires one to pipette a sample by way of a measuring device not associated with the vessel. In sensitive assays prone to contamination, such as antibody diagnostic assays or the polymerase chain reaction (PCR), the use of pipettors or other devices that have been used in other laboratory procedures frequently leads to contamination of the assay and false positive results (*PCR Technology, Principles And Applications For DNA Amplification*, Erlich editor, W. H. Freeman Company Publishers, Page 4, 1992). One-step devices that draw blood by venipuncture and allow the blood to mix with chemicals in an attached reservoir have alleviated some of the contamination problems, but these devices draw a significant volume of blood and are not applicable to sensitive diagnostic tests that require a small amount of sample (Ayres, U.S. Pat. No. 3,874,367). Therefore, a disposable single assembly, diagnostic testing device that can be used for sensitive diagnostic testing without having to introduce a pipette or other measuring device is greatly needed.

SUMMARY OF THE INVENTION

The present invention provides a vial for testing a sample, the vial having a base, a sample delivery sleeve, a sample accessing sleeve, and a cap, wherein the sample delivery sleeve detachably attaches to the base, the sample accessing sleeve detachably attaches to the sample delivery sleeve, and the cap detachably attaches to the sample accessing sleeve. The sample accessing sleeve may include a sample accessing tool, such as, for example, a lancet. The sample delivery sleeve may include a sample delivery member, such as, for example, a capillary tube. The base may contain one or more reagents, such as, for example, a solvent, a buffer, an anticoagulant, an antibody, an enzyme, a dye, a growth nutrient, a marker, and a separation particle. The reagent may also be, or may further include, a magnetic, ferromagnetic, or superparamagnetic substance. The base may also contain at least one additive, such as, for example, sepharose, sephadex, cellulose, sephacryl, acrylic beads, plastic, polycarbonate, polytetrafluoroethylene, glass, polystyrene, polyethylene, polyvinyl, protein, starch, glycogen, chitosan, silica, zeolite, magnetic particles, and diatomaceous earth. The vial or parts thereof may be constructed of a material including, for example, one or more of the following: polyethylene, polypropylene, polystyrene, TEFLON®, polycarbonate, polymethylpentene, TEFZEL®, polytetrafluoroethylene, quartz and glass.

The present invention also provides a method for analyzing a sample, including the steps of: providing a vial for testing a sample, the vial including a base, a sample delivery sleeve, a sample delivery member, a sample accessing sleeve, and a cap, wherein the sample delivery sleeve detachably attaches to the base, the sample accessing sleeve detachably attaches to the sample delivery sleeve, and the cap detachably attaches to the sample accessing sleeve; contacting a material comprising the sample with the sample delivery member to retrieve the sample with the sample delivery member; delivering the sample from the sample delivery member to the base; and analyzing the sample contained within the base. In this method, the sample may include, for example, body fluid and/or body tissue, and the base may contain a reagent. The delivering step may include contacting the sample delivery member with the reagent. The reagent may include, for example, one or more of the following: a solvent, a buffer, an anticoagulant, an antibody, an enzyme, a dye, a growth nutrient, a marker, and a separation particle. The reagent may also be or further include a magnetic, ferromagnetic, or superparamagnetic substance. The delivering step may include rotating the sample delivery sleeve from a first position, in which the sample delivery member does not contact the reagent, into a second position, in which the sample delivery member contacts the reagent. In this method, the sample delivery sleeve may attach to the base in both the first position and the second position.

DETAILED DESCRIPTION OF THE INVENTION

Embodiments of the invention will now be described with reference to the accompanying figures, wherein like numerals refer to like elements throughout. The terminology used in the description presented herein is not intended to be interpreted in any limited or restrictive manner, simply because it is being utilized in conjunction with a detailed description of certain specific embodiments of the invention. The present invention provides advantages that include reliable sampling of a known quantity of body fluid or tissue, the ability to implement diagnostic tests that require the use of a small quantity of sample, and an inexpensive, single assembly that allows for a single use per test so as to minimize contamination.

Figure 1:
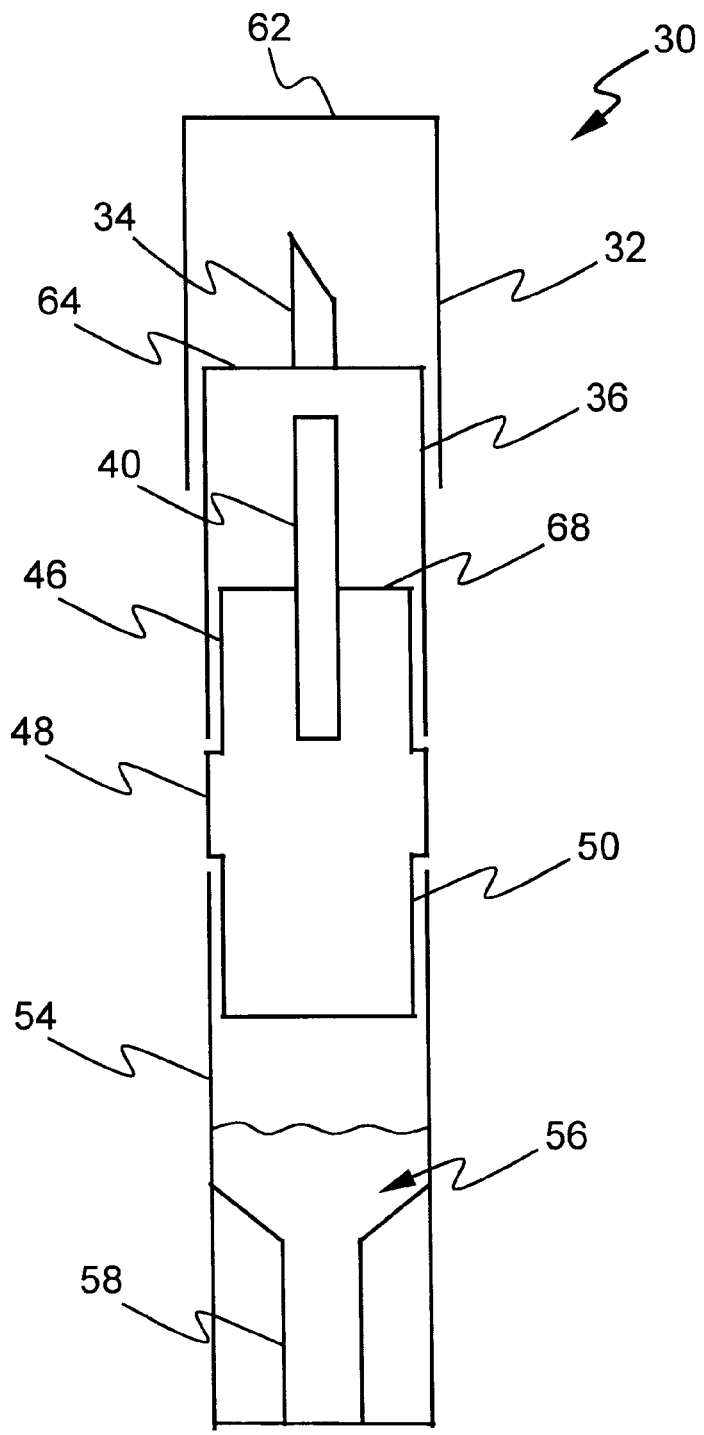
FIG. 1 is a side view of the test vial in a non-used state.
Figure 2:
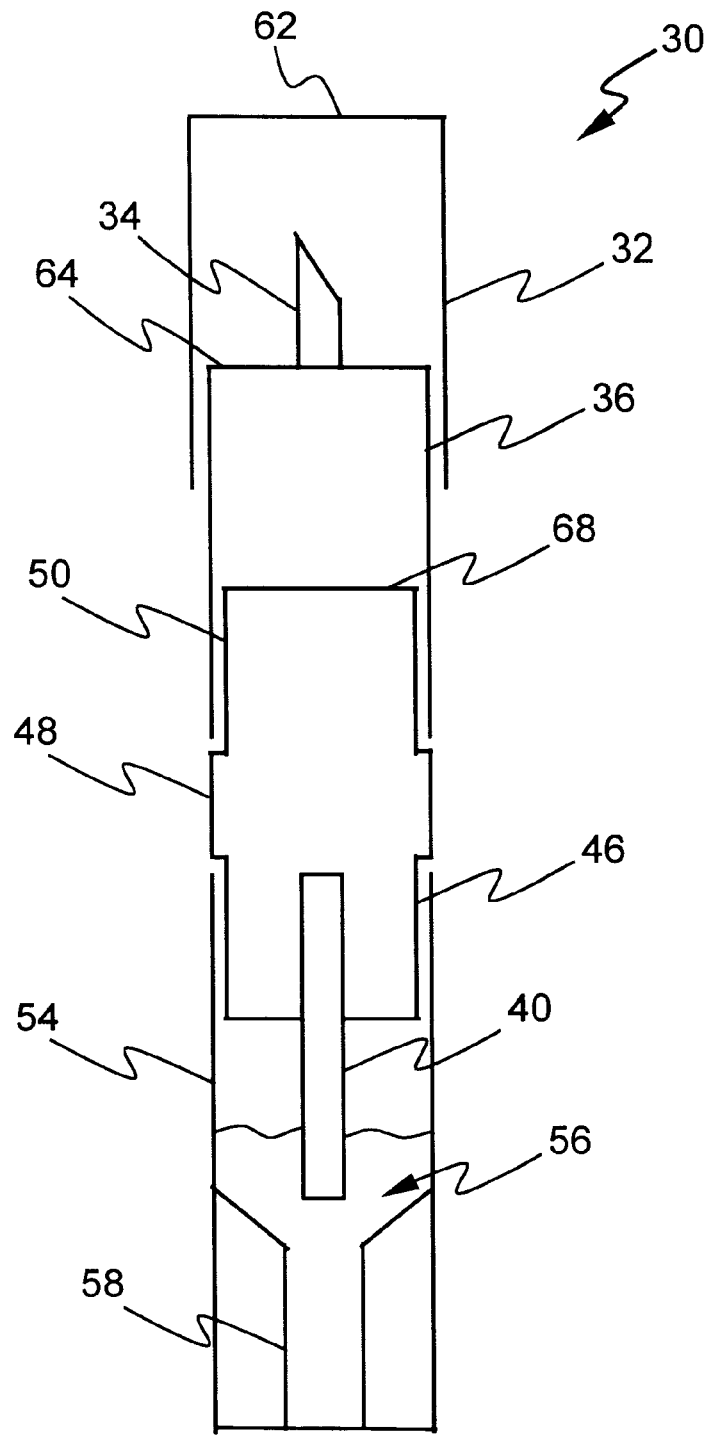
FIG. 2 is the test vial in an activated state.
Figure 3:
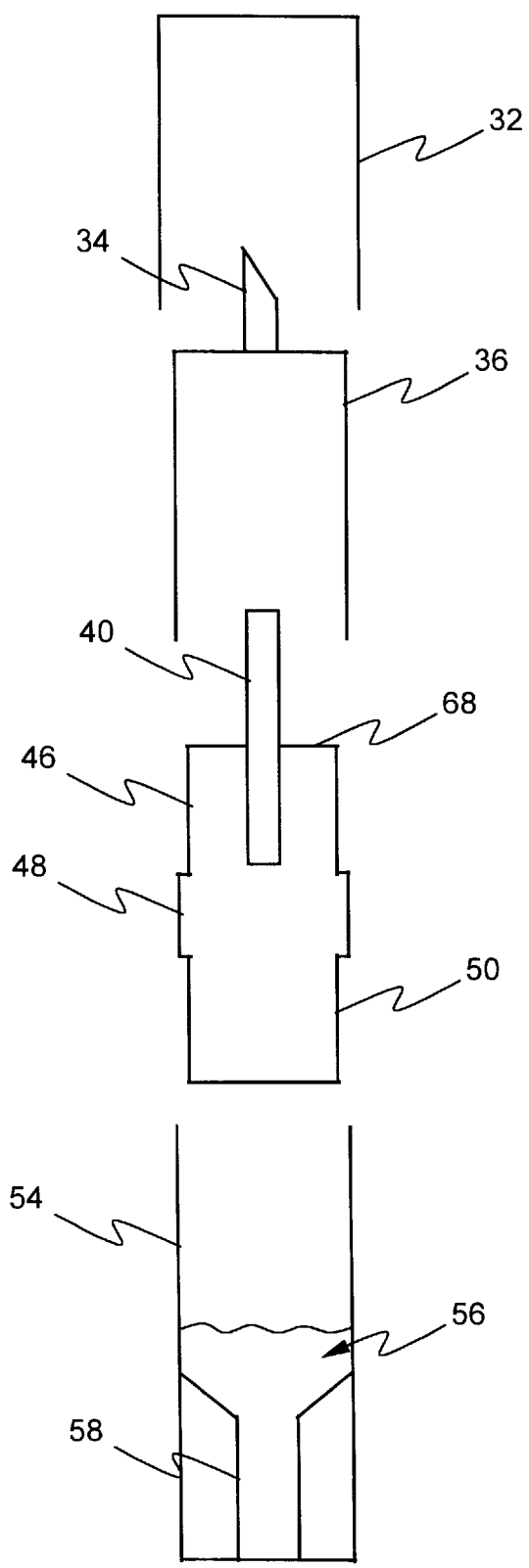
FIG. 3 is an exploded view of the test vial.

As shown in FIGS. 1, 2, and 3, a vial 30 includes a cap 32 that covers a sample accessing tool 34 that is attached to a sample accessing sleeve 36. The sample accessing sleeve 36 covers and protects a sample delivery member 40 that is attached to a sample delivery sleeve 48. The sample delivery sleeve 48 attaches to a base 54 that can contain a reagent 56.

The cap 32 can be of several shapes and is designed to cover the sample accessing tool 34 so as to protect the user from injury and further protect the vial 30 from contamination. In one design, the removable cap 32 is cylindrical, having an open end that fits over the sample accessing sleeve 36, and a closed end 62. The cap 32 can include a flange extending radially therefrom that improves the removability of the cap 32 from the sample accessing sleeve 36. Alternatively, the cap 32 may include a plurality of longitudinal ribs or splines on its surface that extend toward the open end and provide a sufficient textured surface to improve handling and maneuverability of the cap 32 when its being removed from the sample accessing sleeve 36.

The sample accessing sleeve 36 has an open end and a closed end 64. A sample accessing tool 34 is attached to the sample accessing sleeve 36 at the closed end 64. The sample accessing tool 34 can be of several shapes in order to accommodate the type of tissue or body fluid to be sampled. In one embodiment, the sample accessing tool 34 is a lancet as is used in conventional blood sampling instruments. Alternatively, the sample accessing tool 34 can be spoon-shaped and can be used to obtain tissue samples from the cheek or skin, or to obtain fecal samples. Further, a contemplated embodiment includes a sample accessing tool 34 of the shape of a punch or scalpel. The sample accessing tool 34 is mounted to the sample accessing sleeve 36 in a convenient manner such as by epoxy, other adhesive, or during the molding process. The sample accessing tool 34 and sample accessing sleeve 36 can also be a single piece construction.

As shown in FIGS. 1, 2, and 3, the sample accessing sleeve 36 is designed to cover the sample delivery sleeve 48. The sample delivery sleeve 48 comprises a sample delivery member 40 that may be of several shapes and proportions to accommodate the type of testing desired. The sample delivery member 40 may be hollow with a diameter of 50–2000 microns and a length of 1–100 millimeters. Alternatively, the sample delivery member 40 can be spoon-shaped and can be used to obtain tissue samples from the cheek or skin, or to obtain fecal samples.

In one embodiment, the sample delivery member is a capillary tube having a diameter of 400–730 microns and a length of 10–30 millimeters. A capillary tube 40 of this construction would accommodate a fixed volume of about 5–50 microliters. Those of skill in the art will appreciate that the volume of sample that can be drawn into the sample delivery member 40 is directly proportional to the diameter of the sample delivery tube 40 and its length, and that the volume may also be affected by the material of which the delivery tube 40 is composed, the viscosity of the fluid sample, the presence of any lubricants, additives, or stabilizers on the sample accessing tool 34 and/or the delivery tube 40, and the like. Through careful selection of appropriately sized sample delivery members 40, corresponding to exact volumes needed for the quantity of reagent 56 housed in the base 54, many embodiments of the vial 30 can be constructed.

The sample delivery member 40 is mounted into the sample delivery sleeve 48 at a closed end 68 by a conventional method such as epoxy, other adhesive or during the; molding process. The sample delivery member 40 and sample delivery sleeve 48 can also be a single piece construction.

In one embodiment, shown in FIGS. 1, 2, and 3, the sample delivery sleeve 48 is constructed with a first recessed end 46 that allows the sample accessing sleeve 36 to firmly attach to the sample delivery sleeve 48. The sample accessing sleeve 36 and sample delivery sleeve 48 may also be designed to more intimately attach, such as by threads or ridged members. The sample delivery sleeve 48 further includes a second recessed end 50 opposite the first recessed end 46. The second recessed end 50 attaches to the base 54 such that the reagent 56 contained in the base 54 is fully enclosed. In one embodiment, the base 54 and the second recessed end 50 of the sample delivery sleeve 48 contain a plurality of threaded members or a plurality of ridged members so as to provide a tight association. The base 54 is further designed so that it can contain enough reagent 56 to sufficiently react with the volume of sample presented by the sample delivery member 40. The base 54 can be of many designs depending the intended use. As shown in FIG. 1, one embodiment includes a receptacle 58 for the collection of debris, precipitate, resin, superparamagnetic particles, or other particulate matter.

The vial 30 can be constructed of many different materials. The cap 32, sample accessing sleeve 36, sample delivery sleeve 48, and base 54 can be constructed of plastic, polypropylene, polyethylene, polystyrene, TEFLON®, polycarbonate, polytetrafluroethylene, polymethylpentene, TEFZEL®, or any other plastic polymer. In some embodiments, to meet the specific demands of a given diagnostic protocol, parts of the vial can be constructed of other materials, such as, for example, glass or quartz. As for manufacturing, the vial 30, the cap 32, sample accessing sleeve 36, sample delivery sleeve 48, and base 54 are preferably injection-molded from polypropylene or polyethylene. In one embodiment, the cap 32 and sample delivery sleeve 48 are injection-molded from polypropylene, whereas the sample accessing sleeve 36 and base 54 are injected-molded from polyethylene. It is noted that using different materials in corresponding fitting parts can improve the fit between the parts and makes it easier to attach and remove adjoining assemblies.

In a preferred embodiment of the invention for analysis of blood samples, the cap 32, the sample accessing sleeve 36, the sample delivery sleeve 48, and the base 54 are made of polystyrene. These manufacturing techniques and materials, however, are merely exemplary. Various other manufacturing methods and materials could also be used, and could be adapted for a particular use by those of ordinary skill in the art.

The sample accessing tool 34 is preferably made of stainless surgical steel, although glass, TEFLON® or a plastic polymer also can be used. In addition, the sample accessing tool 34 can be advantageously coated with an anti-coagulant such as, for example, heparin. Furthermore, the sample accessing tool 34 can be lubricated to reduce penetration force and thereby reduce pain to the patient during use. The sample delivery member 40 is preferably made of borosilicate glass so that fine volumes of sample can be drawn. Other materials such as metal, TEFLON®, or a plastic polymer can be used in the alternative. Many other materials and manufacturing techniques can be used; the disclosure above is only intended to instruct by way of example.

The reagent(s) 56 housed in the base 54 can be varied. In one embodiment, the reagents can be in a lyophilized or vitreous glass form so as to improve the stability of the reagents. In this case, prior to use, the reagents can be resuspended in water or a suitable buffer prior to introducing the sample delivery member 40 containing the sample to be tested. Alternatively, a body fluid sample can be directly added to the lyophilized or vitreous glass composition of reagents 56 that may advantageously provide an optimal concentration for some assays. Reagents 56 suitable for use in the present invention include, but are not limited to, antibodies, either free or conjugated to a support (such as a resin, affinity chromatography bead, glass particle, silica particle, metal particle, metal oxide particle, or a magnetic or ferromagnetic particle); reagents for use in PCR, cDNA synthesis, or other reactions; proteases (such as RHOZYME® protease); or nutrients that maintain and facilitate the growth of microorganisms. In addition, the reagents 56 may be advantageously conjugated to a marker (such as a superparamagnetic marker, fluorescence marker, dye, enzyme marker, or radioactive marker). Depending on what marker is used, the unopened vial is introduced into an instrument (which measures magnetic properties such as magnetic permeability or remanence, fluorescence, polarization fluorescence, optical activity, light absorbance, enzymatic activity, electrochemical properties, or radioactivity), enabling a qualitative or quantitative analysis. Alternatively, the vial may be opened and subsequently analyzed with conventional technology.

Figure 4:
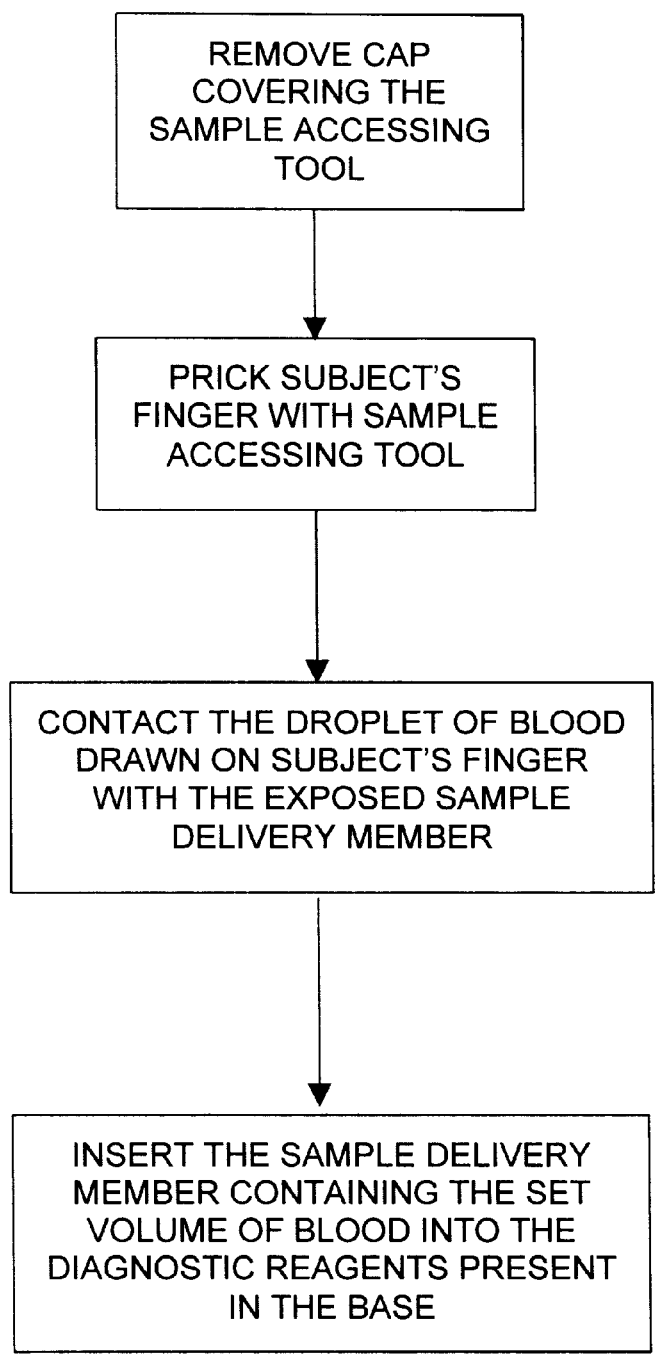
FIG. 4 is a flowchart on the operation of the test vial.

Referring now to FIGS. 1 and 2, and the flowchart illustrated in FIG. 4, the use of the vial 30 of the invention will be discussed. In the inactive configuration displayed in FIG. 1, the sample delivery member 40 is in an upright position proximal to the cap 32. As shown in FIG. 4, a user having the vial 30 first removes the cap 32 to expose the sample accessing tool 34. In one embodiment, the sample accessing tool 34 is sharpened to a point and is used to prick a subject's finger in order to draw a droplet of blood. To prevent injury, the user replaces the cap 32, covering the sample accessing tool 34, and disposes of the cap 32 with the sample accessing sleeve 36 attached in an appropriate waste container. The sample delivery sleeve 48 is then removed from the base 54 and the user contacts the exposed end of the sample delivery member 40 to the droplet of blood on the subject's finger. By capillary action, the droplet of blood is drawn into the sample delivery member 40. The user then inverts the sample delivery member sleeve 48, as shown in FIG. 2, such that the sample delivery member 40 containing the blood sample is contacted with the reagent 56 contained in the base 54. The sample delivery sleeve 48 is kept in this activated state for time sufficient to allow the blood to leave the sample delivery member 40 and enter the pool of reagent 56 in the base 54. A base cap (not shown) can then be placed over the base 54 so that later steps in the test can be performed without contamination or spilling of the contents.

While the above detailed description has shown, described, and pointed out novel features of the invention as applied to various embodiments, it will be understood that various omissions, substitutions and changes in the form and details of the device or process illustrated may be made by those skilled in the art without departing from the spirit of the invention. For example, the invention is not limited to be used in a clinical setting, but may also be used in a broad range of other analytical applications in the human health care industry, such as physicians' in-office analytical uses, mass screenings, home screening kits, and the like. Also contemplated is use of the invention in veterinary medicine, the food industry and agriculture, chemical engineering and synthesis, environmental testing, pharmaceuticals, cosmetics, and other fields wherein it is desirable to conveniently obtain samples for analysis. In these varied applications, the invention can be used to analyze fluids, suspensions, gels, semisolids, and solids, whether biological or non-biological. In some of these applications the sample accessing tool 34 may not be needed, or may be substituted for a different component. The appropriate component for any particular use can be determined readily by those of ordinary skill in the art As is also stated above, it should be noted that the use of particular terminology when describing certain features or aspects of the present invention should not be taken to imply that the terminology is being redefined herein to be restricted to including any specific characteristics of the features or aspects of the invention with which that terminology is associated. The scope of the invention is indicated by the appended claims and their equivalence rather than by the foregoing description.

What is claimed is:

1. A vial for testing a sample, comprising:
   a base, a reversible sample delivery sleeve comprising a sample delivery member, a sample accessing sleeve, and a cap, wherein the sample accessing sleeve detachably attaches to the sample delivery sleeve, and the cap detachably attaches to the sample accessing sleeve, and wherein the sample delivery sleeve detachably attaches to the base in a first and a second orientation, wherein in the first orientation the sample delivery member extends away from the base, and wherein in the second orientation the sample delivery member is positioned within the base.

2. The vial of claim 1, wherein the sample accessing sleeve comprises a sample accessing tool.

3. The vial of claim 2 wherein the sample accessing tool is a lancet.

4. The vial of claim 3, wherein the sample delivery member is a capillary tube.

5. The vial of claim 1, further comprising a reagent within the base.

6. The vial of claim 5 wherein the reagent comprises one or more of the group consisting of a solvent, a buffer, an anticoagulant, an antibody, an enzyme, a dye, a growth nutrient, a marker, and a separation particle.

7. The vial of claim 6 wherein the reagent further comprises a ferromagnetic substance.

8. The vial of claim 1, further comprising at least one additive within the base.

9. The vial of claim 8 wherein the additive is selected from the group consisting of sepharose, sephadex, cellulose, sephacryl, acrylic beads, plastic, polycarbonate, polytetrafluoroethylene, glass, polystyrene, polyethylene, polyvinyl, protein, starch, glycogen, chitosan, silica, zeolite, magnetic particles, and diatomaceous earth.

10. The vial of claim 1, wherein the base is constructed of a material comprising at least one member selected from the group consisting of polyethylene, polypropylene, polystyrene, TEFLON®, polycarbonate, polymethylpentene, TEFZEL®, polytetrafluoroethylene, quartz and glass.

11. A method for analyzing a sample, comprising the steps of:
- providing a vial for testing a sample, the vial comprising a base, a reversible sample delivery sleeve comprising a sample delivery member, a sample accessing sleeve, and a cap, wherein the sample accessing sleeve detachably attaches to the sample delivery sleeve, and the cap detachably attaches to the sample accessing sleeve, and wherein the sample delivery sleeve detachably attaches to the base in a first and a second orientation, wherein in the first orientation the sample delivery member extends away from the base, and wherein in the second orientation the sample delivery member is positioned within the base;
- contacting a material comprising the sample with the sample delivery member to retrieve the sample with the sample delivery member;
- delivering the sample from the sample delivery member to the base; and
- analyzing the sample contained within the base.

12. The method of claim 11, wherein the sample comprises body fluid.

13. The method of claim 11, wherein the sample comprises body tissue.

14. The method of claim 11, wherein the base contains a reagent, and wherein the delivering step comprises contacting the sample delivery member with the reagent.

15. The method of claim 14 wherein the reagent comprises one or more of the group consisting of a solvent, a buffer, an anticoagulant, an antibody, an enzyme, a dye, a growth nutrient, a marker, and a separation particle.

16. The method of claim 15, wherein the reagent further comprises a ferromagnetic substance.

17. The method of claim 11 wherein the delivering step comprises rotating the sample delivery sleeve from a first position, in which the sample delivery member does not contact the reagent, into a second position, in which the sample delivery member contacts the reagent.

18. The method of claim 17 wherein said sample delivery sleeve attaches to the base in both said first position and said second position.

* * * * *